United States Patent [19]

Hogan et al.

[11] Patent Number: 5,030,557
[45] Date of Patent: Jul. 9, 1991

[54] MEANS AND METHOD FOR ENHANCING NUCLEIC ACID HYBRIDIZATION

[75] Inventors: James J. Hogan; Curt L. Milliman, both of San Diego, Calif.

[73] Assignee: ML Technology Venture, New York, N.Y.

[21] Appl. No.: 124,975

[22] Filed: Nov. 24, 1987

[51] Int. Cl.$^5$ .......................... C12Q 1/68; C12P 1/04; C07H 19/06; G01N 33/566

[52] U.S. Cl. ........................ 435/6; 435/170; 435/810; 436/501; 536/26; 536/27; 536/28; 935/77; 935/78

[58] Field of Search ............ 435/6, 170, 810; 436/501; 536/27, 28, 26; 935/77, 78

[56] References Cited

U.S. PATENT DOCUMENTS 4,717,653  1/1988  Webster, Jr. .......................... 435/35
4,851,330  7/1989  Kohne .................................. 436/94
4,883,750  11/1989  Whiteley et al. ..................... 935/78

Primary Examiner—Robert A. Wax
Assistant Examiner—Stephanie W. Zitomer
Attorney, Agent, or Firm—Lyon & Lyon

[57] ABSTRACT

The binding of a nucleic acid probe with its complementary sequence in a targeted, single stranded nucleic acid is affected by the secondary and tertiary structure of the target nucleic acid. The rate and extent of hybridization of the probe with the targeted nucleic acid can be increased by the use of "helper" oligonucleotides. Helper oligonucleotides are selected to bind to the target nucleic acid and impose a different secondary and tertiary structure on the target to facilitate the binding of the probe to the target. The resulting hybrid of probe and target nucleic acid also exhibits a higher $T_m$ than the hybrid which results from addition of the probe alone.

27 Claims, 3 Drawing Sheets

SECONDARY STRUCTURE OF EUBACTERIAL 16S RIBOSOMAL RNA

ESCHERICHIA COLI

MEANS AND METHOD FOR ENHANCING NUCLEIC ACID HYBRIDIZATION

FIELD OF THE INVENTION

This invention relates to methods for enhancing hybridization between a polynucleotide and a nucleotide multimer complementary to a nucleotide sequence within the polynucleotide. In another aspect, it relates to diagnostic assays and therapeutic processes using nucleic acid probes.

BACKGROUND

Nucleic acid hybridization, the formation of a double strand of nucleic acids by formation of hydrogen bonds between complementary strands of nucleic acids, is a well known phenomenon finding increasing application. For example, hybridization is the core phenomenon of so-called "genetic probe" assays. Thus, an assay to confirm the presence in a suitably prepared sample of a nucleic acid of diagnostic significance can be built around a nucleic acid, usually an oligonucleotide (oligomer) of known sequence (the "probe") which is complementary to a nucleotide sequence within the targeted nucleic acid. See, for example, U.S. Pat. No. 4,358,535.

The formation of hybrid between the probe and targeted nucleic acid, usually detected by a suitable label linked to the probe after separation of unbound probe, is taken as confirmation that the complementary sequence is present in the nucleic acid of the sample. The presence of this sequence, if properly selected, permits inferences of diagnostic significance to be drawn. For example, if the sequence complementary to the probe is unique to a genus or species of bacteria which causes disease, the presence of the genus or species in the sample is confirmed if hybrid formation is detected. Absence of hybrid formation, on the other hand, permits the negative inference, i.e., that the sample does not contain the suspect organism (or organisms), at least within the detection limits of the assay. Such an assay might be used with other symptomatology to diagnose that disease is present or that disease is caused by the detected organism. A similar assay might show its presence in food intended for human consumption. Using similar techniques, nucleic acid probes can be used to detect not only bacteria, but also disease causing fungi, viruses, oncogenes or protooncogenes, genes associated with a variety of genetic diseases, and the like.

It has also been proposed to use nucleic acid probes therapeutically. For example, if a cell is infected by a virus, and a probe is introduced into the cell which is complementary to at least a portion of the messenger RNA (mRNA) encoded by the virus or to its genomic nucleic acid, binding of the probe to the targeted viral nucleic acid would prevent its transcription or translation by the cell's ribosomes, effectively preventing the virus from replicating. This phenomenon of probe hybridization with mRNA is referred to as "hybridization arrest." Hybridization arrest using a methylphosphonate derivative of DNA as a probe is described in U.S. Pat. No. 4,511,713. The use of hybridization arrest techniques to inhibit mRNA translation of dihydrofolate reductase in an in vitro model using anti-sense oligonucleotides, including mixtures of short oligonucleotide sequences, is described by Maher, et al., *Archives of Biochem. and Biophys.*, 253, 214–20 (1987).

In the case of using genetic probes to detect organisms, particularly infectious organisms, it has heretofore been the general practice to target DNA in order to identify the organisms of interest. Because DNA is already double stranded, this has made it necessary to not only lyse the cell to liberate the DNA, but also to denature (melt) the double stranded DNA to obtain a single stranded structure. This is typically done by heating the double stranded DNA to a temperature at which the duplex structure comes completely apart. The temperature at which this occurs in solution can vary. The $T_m$ of a duplex (the temperature at which 50% of the strands of DNA have separated) is increased by increasing the ionic strength of the solution and decreases in the presence of reagents such as formamide which destabilize hydrogen bonds.

After denaturation, the DNA is typically fixed to a solid surface such as nitrocellulose to preclude reformation of the DNA's binary structure (renaturation) by hybridization of the separated strands. See U.S. Pat. No. 4,358,535. While fixing the DNA to a solid surface prevents renaturation, it imposes heterogeneous kinetics, with their attendant disadvantages including a much slower rate of hybridization, on the assay system. Fixing the DNA to a solid surface also may fix the DNA in an orientation which prevents hybridization with the probe.

To overcome these limitations it has been proposed to conduct hybridization in solution since solution kinetics are much more favorable than heterogeneous kinetics. As a result, hybridization goes to completion in solution much faster than would be the case if the targeted DNA is fixed to a solid surface. In-solution hybridization can be carried out by adding probe to the denatured DNA and reestablishing conditions under which duplex formation can occur. If a sufficient excess of probe is used, it can compete effectively for the particular nucleotide sequence in the targeted nucleic acid to which the probe is directed with the DNA present in the sample that is complementary to that sequence.

At least some of the problems associated with targeting DNA can be avoided by using RNA as a target. RNA is already single stranded and, therefore, the necessity for denaturing and fixing the DNA to a solid phase or carrying out hybridization under conditions in which the probe must compete with the organism's own DNA is eliminated. In the case of viruses, mRNA can be a useful target. However, in the case of pro-and eucaryotes, it is preferred to target ribosomal RNA (rRNA) since each cell contains about $10^{3-10^4}$ as much rRNA target sites as genomic DNA. Thus targeting rRNA, if available as a target, permits assays of much greater sensitivity.

Assay methods which target RNA and exploit in-solution hybridization are described in Canadian Patent No. 1,215,904 and European Patent Application No. 84900667.1, the disclosures of which are incorporated herein by reference.

Although much more convenient for the user, the development of assays which target ribosomal RNA presents problems. Often a candidate probe, which otherwise appears to be ideal, fails because it exhibits a very slow reaction rate or poor extent of reaction, even when hybridization is carried out in solution. As a result, it may in some cases be necessary to select for an assay a probe which compromises specificity in order to achieve the desired kinetics. In other cases, it may be necessary to sacrifice sensitivity in order to achieve a commercially viable assay because of the slow kinetics or poor extent of hybrid formation.

Approaches to accelerating the rate of hybridization of complementary nucleotide multimers have been explored. Among those are the addition of nucleic acid precipitating reagents to the hybridization solution as described in application for U.S. application Ser. No. 57,981, filed June 4, 1987, assigned to the assignee of this application and the disclosure of which is incorporated by reference as if fully set forth herein.

The use of rate acceleration techniques as described in the above-referenced application does not in every case provide a rate of hybridization increase which permits optimal assay development. As a result, there remains a need for other means of enhancing the kinetics of hybridization between a probe and its target sequence which can be used with, or even in lieu of, other techniques for accelerating the rate of hybridization between complementary nucleotide multimers.

Another problem is sometimes encountered in the development of assays of narrow specificity, particularly when the assay is directed to a single species of an organism in a genus containing closely related species. The sequence homology of the genomic DNA and ribosomal RNA of the target species and its close relatives is very close in such cases and these nucleic acids often contain mismatches of only one or two nucleotide bases in relatively long sequences.

With the advent of nucleic acid synthesizers, it has been possible to design and synthesize probes which are a perfect, or near perfect, complement for a sequence in the targeted nucleic acid. The $T_m$ of a hybrid between the probe and its complement in the targeted nucleic acid is a function of the number of complementary nucleotides involved in hybrid formation, i.e., as the length of the probe increases so generally does the $T_m$. Therefore, the probe must be long enough so that a stable hybrid is formed at the temperature at which the assay is carried out.

This temperature is selected so that the extent of hybridization within a reasonable time is enough to give the assay adequate sensitivity. Often a probe long enough to permit this has sufficient complementarity with a sequence in one or more closely related species that significant hybridization with the nucleic acid of the closely related species can also occur during the assay. This cross reactivity is usually due to the fact that their melting profiles are overlapping. This can reduce the specificity of the assay by causing false positive results. Cross reactivity could be significantly reduced or even avoided, however, if the $T_m$ of relatively short probes could be raised since the difference in $T_m$ between a hybrid of a probe and its perfect match and a hybrid of the probe with a nucleic acid having one or more nucleotide mismatches is usually greater for a short probe compared to a larger one having the same number of mismatches. The shorter probe has a higher percentage of mismatches to its nearest neighbor than the longer probe which can result in their melting profiles no longer overlapping. This larger difference in the $T_m$ means that the mismatched hybrid can be completely dissociated while the percentage of hybridization of probe to target remains high. Reduction in such cross reactivity would, of course, have the result of reducing or eliminating false positive results with a resulting increase in assay specificity.

SUMMARY OF THE INVENTION

A single stranded nucleic acid such as rRNA or denatured DNA has an ordered secondary structure arising from intramolecular formation of hydrogen bonds between complementary nucleotide sequences within the single stranded nucleic acid itself. These sequences can be brought into close enough proximity to permit intramolecular hybridization by chain folding. The result is a structure like that depicted in FIG. 1 which is a depiction of the secondary structure of the eubacterial 16S rRNA in which the "dots" represent individual nucleotides and the "dashes" represent intramolecular hydrogen bonds. Although not shown in FIG. 1, the rRNA also possesses tertiary structure arising from the same kind of attractive forces that order duplex DNA into its now well known helical structure.

A substantial portion of this secondary and tertiary structure is not lost under conditions normally employed for nucleic acid hybridization, e.g., elevated temperature, presence of salt, presence of accelerators and the like. We have found that this residual structure can sterically inhibit, or even block, hybrid formation between a nucleotide multimer, for example a DNA or RNA oligomer being used as a probe, and its complementary sequence in the ribosomal RNA or other single stranded nucleic acid such as mRNA or DNA which the probe targets. We have further found that this inhibition can be reduced and even eliminated, by use of a "helper" oligonucleotide which binds to a portion of the RNA or DNA other than that being targeted by the probe, and which imposes new secondary and tertiary structure on the targeted region of the single stranded nucleic acid whereby the rate of binding of the probe is accelerated. Thus, by using a properly selected helper oligonucleotide, the rate of hybridization between the probe and its complementary sequence in the targeted nucleic acid can be substantially increased and even permit hybridization to occur at a rate and under conditions otherwise adequate for an assay where, without the use of the helper, no substantial hybridization can occur.

We have also found that the use of a helper can raise the $T_m$ of the hybrid of a relatively short probe and its intended target relative to the $T_m$ of the hybrid of the probe and a nucleic acid sequence with which the probe is less complementary. As a result, assays for organisms which occur in environments populated by closely related organisms can be obtained which exhibit improved specificity.

Accordingly, an object of the invention is to facilitate binding between a targeted single stranded nucleic acid, however derived, which has sufficient higher order secondary structure to inhibit binding of a nucleotide multimer complementary to a nucleotide sequence within the targeted nucleic acid.

Another object of the invention is to provide improved assays which target ribosomal RNA or other nucleic acids by affording a greater selection of nucleotide multimer probes having properties useful in the assays.

Another object of the invention is to enhance the performance of assays which utilize nucleotide multimer probes complementary to sequences within targeted RNA or other nucleic acid by accelerating the rate of hybridization between probe and target.

The achievement of these and other objectives will be described in the following Detailed Description of the Invention and with reference to the drawings.

DESCRIPTION OF PREFERRED EMBODIMENTS

Figure 1:
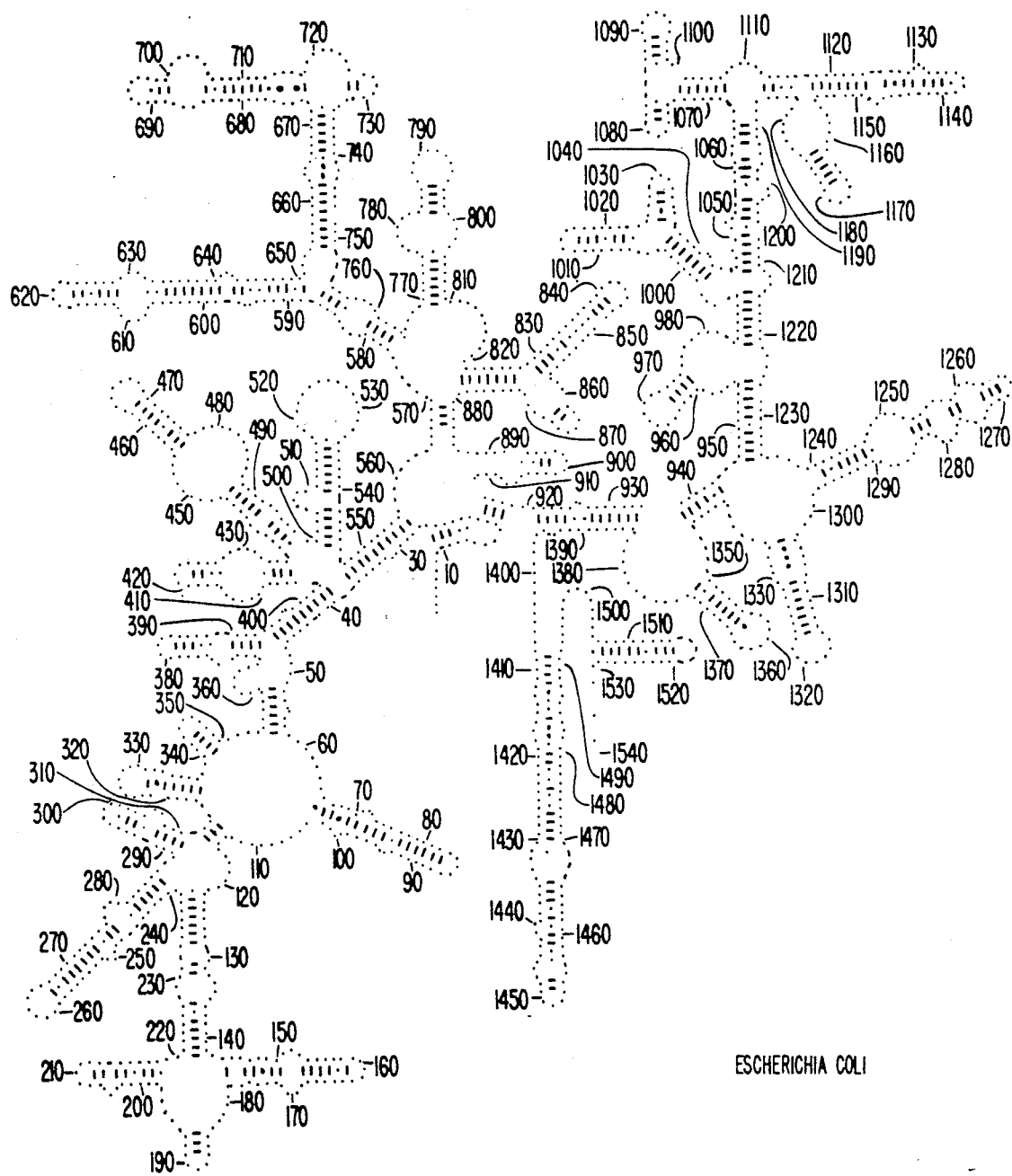
FIG. 1 is an illustration of the secondary structure of the eubacterial 16S ribosomal RNA.

As used in this disclosure, the following terms are defined as:

nucleotide: a subunit of a nucleic acid consisting of a phosphate group, a 5 carbon sugar and a nitrogen containing base. In RNA the 5 carbon sugar is ribose. In DNA, it is 2-deoxyribose.

nucleotide multimer: a chain of nucleotides linked by phosphodiester bonds.

oligonucleotide or oligomer: a nucleotide multimer generally about 10 to about 100 nucleotides, but which may be 200 or more nucleotides in length. They are usually synthesized from nucleotide monomers or obtained by enzymatic means.

polynucleotide: a nucleotide multimer generally about 100 nucleotides or more in length. complementarity: a property conferred by the base sequence of a single strand of DNA or RNA which, with another DNA or RNA strand, may form a hybrid of double stranded DNA:DNA, RNA:RNA or DNA:RNA through hydrogen bonding between Watson-Crick base pairs on the respective strands. Adenine (A) usually complements thymine (T) or uracil (U), while guanine (G) usually complements cytosine (C). Non-canonical base pairs, for example, A:G or G:U, can also lend stability to a double strand.

nucleotide probe: a nucleotide multimer having a nucleotide sequence complementary with a sequence in a targeted nucleic acid, usually a polynucleotide, having diagnostic or therapeutic significance. Usually the probe is selected to be perfectly complementary to the target sequence. However, in some cases it may be adequate or even desirable that one or more nucleotides in the probe not be complementary to the corresponding base in the target sequence. A nucleotide probe is also usually a smaller multimer than the multimer containing the target sequence. Typically it is an oligonucleotide, but may be a polynucleotide, and for assay procedures is usually labeled with a chemical substituent which permits its detection, for example, by radiometric, colorimetric, fluorometric, chemiluminescence or other suitable techniques. In appropriate cases, the probe may be an analogue of the phosphate ester structure of typical DNA or RNA. For example, it may have an alkyl or phosphate, a phosphorothioate or other modified backbone structure.

helper oligonucleotide: a nucleotide multimer, generally not greater than about 50 nucleotides in length, which binds the targeted nucleic acid without substantially overlapping the region bound by a nucleotide probe and which enhances the kinetics of hybridization between the probe and the sequence within the targeted nucleic acid with which it is complementary and/or which raises the Tm of the hybrid between probe and complementary sequence.

As pointed out in the Summary of the Invention, we have found that the binding between a nucleotide probe and a sequence with which it is complementary found in a targeted nucleic acid can be enhanced by use of an oligonucleotide helper in the sense that the rate and extent of hybridization can be increased. In some cases where the unassisted probe does not show measurable hybridization with the target, use of a helper oligonucleotide permits the probe to bind efficiently with its complementary sequence within the target nucleic acid. We have also found that the use of a helper oligonucleotide can raise the $T_m$ of a hybrid formed by the probe and target nucleic acid. Accordingly, when reference is made to enhancement of binding herein, that means that the rate of hybridization and/or extent of hybridization is increased and/or the $T_m$ of the resulting hybrid is increased. As will be apparent from the following discussion, these observations have significant practical application.

Also as pointed out in the Summary of the Invention, the effect of helper oligonucleotides on the kinetics of hybridization is the result of reordering of the secondary and tertiary structure of the single stranded targeted nucleic acid. Thus, the invention is useful in improving the kinetics of hybridization between a probe and a nucleic acid selected from DNA or RNA. Targeted DNA may be of any origin, including, but not limited to, genomic DNA of cells such as unicellular microorganisms or cells from higher life forms or the nucleic acid of viruses. Similarly, targeted RNA may be of any origin including, but not limited to, that found in cells as mRNA, rRNA or tRNA. Accordingly, in appropriate circumstances, the targeted nucleic acid may be associated with a virus, a tumor cell, a cell evidencing genetic disease, or an organism which causes disease.

The probe is typically a relatively short nucleotide multimer of either RNA or DNA, the latter being preferred because of the difficulty of protecting RNA probes from degradation by highly stable and efficient enzymes which breakdown RNA. The probes may also be analogues of the phosphate diester backbone of DNA or RNA in their usual forms. For example, in certain applications such as hybridization arrest procedures, the probe may be a methylphosphonate analogue of DNA as described in U.S. Pat. No. 4,511,713, or other alkyl or arylphosphonates as described in U.S. Pat. Nos. 4,507,433 and 4,469,863, or a phosphorothioate analogue as described in Matsukura, et al., "Phosphorothioate Analogs of Oligodeoxynucleotides: Novel Inhibitors of Replication and Cytopathic Effects of Human Immunodeficiency Virus (HIV)," PNAS, (In press).

Currently preferred for use in the invention are oligonucleotide probes which are generally of about 10 to about 50 nucleotides in length and, preferably, from about 15 to about 40 nucleotides in length. Such probes are conveniently obtained using a DNA synthesizer and are generally designed to be perfectly complementary to a nucleotide sequence within the target nucleic acid. However, a perfect nucleotide match is not always necessary and in some cases advantages can be obtained by deliberately introducing non-canonical base pairs or mismatches.

Usually the probe is selected to bind a region within the target nucleic acid so as to minimize cross reaction with a nucleic acid whose hybridization with the probe would be undesirable. In other words, the probe is selected to bind the target nucleic acid in a region where a closely related nucleic acid has the least homology. For example, in the case of a probe for use in a diagnostic assay for a species or group of organisms, the probe is selected to bind to DNA or RNA associated with the organism or organisms of choice in a region which exhibits the greatest evolutionary divergence from the nearest phylogenetic relative which may contaminate a sample containing the target organism or organisms.

The helper oligonucleotide is selected to bind to the target nucleic acid in a region which affects the kinetics of hybridization between the probe or target nucleic acid by increasing the rate of hybridization and extent of binding and/or which raises the $T_m$ of the resulting hybrid. In some cases, the helper oligonucleotide may be selected to bind a region in the target nucleic acid which is immediately adjacent to that bound by the probe. In such a case limited overlap between the region recognized by the helper and that recognized by the probe can be tolerated but is usually not desirable. In other cases the helper may exhibit the desired effect even though it binds a region removed from that bound by the probe.

Like the probes, helper oligonucleotides can be DNA or RNA, DNA being preferred for reasons already indicated. Also, the helper oligonucleotides can be analogues of phosphate diesters such as the alkyl or aryl phosphonates and phophorothioates previously mentioned.

Helper oligonucleotides are also conveniently obtained by synthetic means and are usually within the range of about 10 to about 100 nucleotides in length. Preferred helpers are from about 20 to about 50 nucleotides in length because larger helpers are difficult to synthesize and shorter helpers are less effective in achieving the desired effects. The helper probe need not be designed to have a nucleotide sequence which is not complementary to nontarget nucleic acid since the ability to discriminate between target and nontarget nucleic acids is the function of the probe. However, if the region to which the helper oligonucleotide binds also exhibits less than perfect sequence homology with closely related nontarget nucleic acid, the helper may enhance the discrimination between target and nontarget.

Hybridization of probe to target nucleic acid may be carried out under conditions where the probe concentration and that of target are the same or in probe or target excess. When the probe is used in excess, it is typically used in a molar concentration which is at least about 5 to about 20 or more times that of the target.

Usually the helper oligonucleotide is used in excess compared to the probe. When the probe is used in excess to the target nucleic acid, the helper oligonucleotide is typically used in a molar concentration at least about 5 times that of the probe and up to a molar concentration which is about 100 or more times that of the probe. When target is in excess compared to probe, the helper oligonucleotide typically is used in a molar concentration at least about 10 times that of the target and up to about 100 or more times that of the probe.

By the utilization of a helper oligonucleotide, it has been possible to increase the rate of hybridization of a probe to target nucleic acid by as much as 100 fold or more. It has also been possible to increase the extent of hybridization no matter how long one runs the reaction and to raise the $T_m$ of the hybrid of probe and target nucleic acid. The following examples demonstrate those effects:

EXAMPLE 1

The 16S rRNA of Salmonella exhibits a typical closed intrastrand, helical structure in the 430–500 region of the 16S ribosome. A probe for this region was constructed using a DNA synthesizer having the following nucleotide sequence:

5'-TGCGGTTATTAACCACAACACCTT-3'

Assays for *Salmonella enteritidis* were run using this probe with and without helper oligonucleotides selected from the following:

Helper A: 5'-CCTCCCCGCTGAAAGTACTTTAC-3'

Helper B: 5'-GGTGCTTCTTCTGCGGGTAACGTCAAT-GAG-3'

Figure 2:
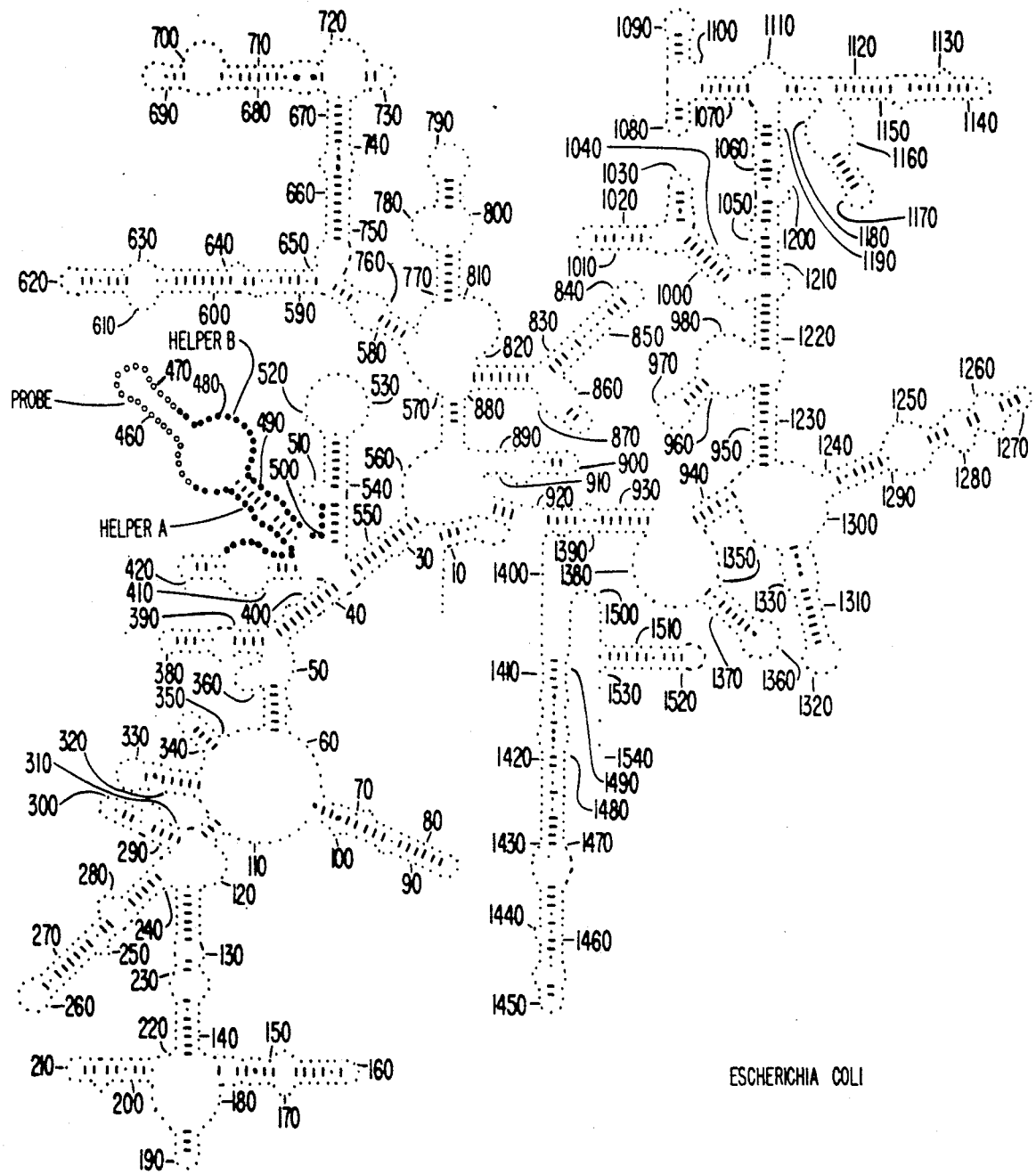
FIG. 2 is an illustration of the secondary structure of the eubacterial 16S ribosomal RNA showing the binding locations of a probe for *Salmonella enteritidis* and two helper oligonucleotides according to the invention.
Figure 3:
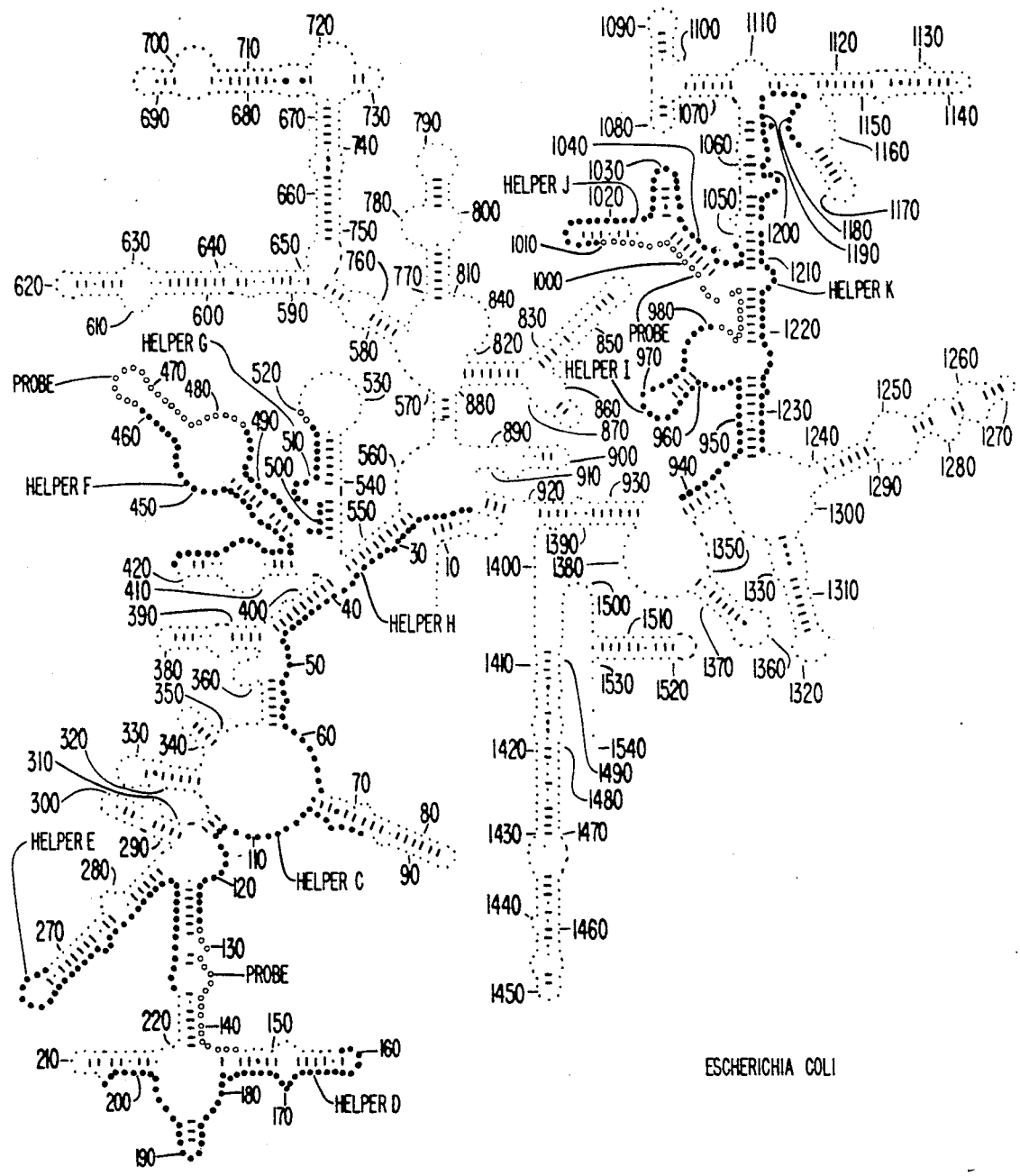
FIG. 3 is an illustration of the secondary structure of the eubacterial 16S ribosomal RNA showing the binding locations of probes and helper oligonucleotides for *Neisseria gonorrhea* according to the invention.

Helper A and Helper B were selected to bind to the rRNA of Salmonella in the regions immediately adjacent to the probe as shown in FIG. 2, Helper A binding in about the 430–450 region and Helper B in about the 480–510 region.

The assays were run under the following conditions: $^{32}$P-end labeled probe was combined with 0.1 microgram of target rRNA in target excess. The hybridization was run at 55° C .in 100 microliters of 0.48 M sodium phosphate buffer containing 0.5% sodium dodecyl sulfate, 1 mM EDTA and 1 mM EGTA. When helper was used, the molar concentration of helper was 100 times that of the probe. When two helpers are used, each was in a molar concentration 100 times that of the probe. The hybridized probe was separated from unhybridized probe using hydroxyapatite as described in Canadian Patent No. 1,215,904 and the hybrids quantitated by scintillation counting.

Table I below shows the percent of hybridization of the probe to *Salmonella enteritidis* rRNA obtained under assay conditions using the probe alone and with either Helper A or Helper B or with both together.

TABLE I

| | % Hybrid Found | |
|---|---|---|
| Reagent | Hybridization for 6 min. | Hybridization Overnight |
| Probe Alone | 1.2% | 1.8% |
| Probe/Helper A | 26.3% | 68.5% |
| Probe/Helper B | 51.6% | 68.0% |
| Probe/Helpers A and B | 78.6% | 83.1% |

The results shown in Table I demonstrate the dramatic effect on probe hybridization with a target nucleic acid which can be obtained using a helper oligonucleotide. In each case nearly significant hybridization was obtained when the helpers were used under conditions where less than 2% hybridization of the probe was observed in the absence of helper.

The $T_m$ of the hybrids which resulted from the hybridization of the probe with *Salmonella enteriditis* with and without assistance of a helper oligonucleotide were also determined in 0.12 M phosphate buffer containing 0.02% sodium dodecyl sulfate and lmM EDTA and 1 mM EGTA. The $T_m$ of the probe alone was 59° C. By comparison, the $T_m$ with Helper A was 63.5° C. and with Helper B, 63° C.

EXAMPLE 2

Neisseria also exhibits closed intrastrand, helical structures in the 16S ribosome. We found examples in the 130–150, 460–480 and 980–1010 regions. A probe for the 130–150 region was synthesized using a DNA synthesizer having the following nucleotide sequence:

5'-CCGCTACCCGGTACGTTC-3'

Assays for *Neisseria gonorrhea* were run using this probe with and without helper oligonucleotides selected from the following:

Helper C:
5'-CGATATGTTACTCACCCGTTCG-
CCACTCGCC-3'

Helper D:
5'-CCCCTGCTTTCCCTCTCTAGACG-
TATGCGGTATTAGCTGATCTTTCG-3'

Helper E:
5'-GGCCTTTACCCCGCCAACCAGCTAAT-
CAGA0TATCGGCCGCTC-3'

Helper C was selected to bind to the rRNA of Neisseria in the region immediately adjacent to the probe as shown in FIG. III, in a region centering at about 110. Helpers D and E were selected to bind in regions of the rRNA remote from that bound by the probe as also shown in FIG. III. Helper D is centered at about 190 and Helper E at about 250.

The assays were run under the same conditions as Example 1, including the same molar ratios of helper (or helpers) to probe, except that hybridization was carried out at 60° C. The $T_m$'s of the hybrids were also obtained as in Example 1.

Table IIA below shows the percent of hybridization of the probe to *Neisseria gonorrhea* rRNA under assay conditions using the probe alone and with each helper and combinations of helpers.

TABLE IIA

| | Percent Hybrid Found | | |
| Reagent | Hybridization for 12 min. | Overnight Hybridization | Tm |
| --- | --- | --- | --- |
| Probe alone | 1% | 9% | 62.4° C. |
| Probe & Helper C | 18% | 75% | 65.9° C. |
| Probe & Helper D | 7% | 65% | 63.4° C. |
| Probe & Helper E | 7% | 22% | 63.0° C. |
| Probe & Helpers C & D & E | 22% | 85% | 66.0° C. |
| Probe & Helpers C & E | 22% | 77% | 65.5° C. |
| Probe & Helpers C & D | 21% | 85% | 65.7° C. |
| Probe & Helpers D & E | 8% | 62% | 63.3° C. |

Probes and helper oligonucleotides were also synthesized for the 460–480 region and for the 980–1010 region. Assays were run at 60° C. and $T_m$'s determined as in Example 1. The binding locations of the probes and helpers are shown in FIG. III. The results are shown in Tables IIB and IIC, respectively.

TABLE IIB

| | Percent Hybrid Found | | |
| Reagent (& Sequence) | Hybridization for 12 min. | Overnight Hybridization | Tm |
| --- | --- | --- | --- |
| Probe alone (TCATCGGCCGCCGATATTGGC) | 0.8% | 10% | 62.8° C. |
| Probe & Helper F (AACGGCCTTTTCTTCCCTGA-CAAAAGTCCTTTACAACCCG) | 4% | 68% | 64.9° C. |
| Probe & Helper G (GGCACGTAGTTAGCCGGTGCTT-ATTCTTCAGGTACCG) | 12% | 72% | 67.5° C. |
| Probe & Helper H (CGACTTGCATGTGTAAAGCTT-GCCGCCAGCGTTCAATCTGAGCC) | 0.9% | 10 | |
| Probe & Helpers F & G & H | 11% | 85% | 69.5° C. |
| Probe & Helpers F & G | 9% | 83% | 69.5° c. |

TABLE IIC

| | Percent Hybrid Found | | |
| Reagent (& Sequence) | Hybridization for 12 min. | Overnight Hybridization | Tm |
| --- | --- | --- | --- |
| Probe alone (GAGGATTCCGCACATGTCAAA-CCAGGTAA) | 7% | 63% | 59.2° C. |
| Probe & Helper I (GGTTCTTCGCGTTGCATCG-AATTAATCCACATCATCCACCGC) | 16% | 78% | 61.5° C. |
| Probe & Helper J (CCTGTGTTACGGCTCCCGAAGG-CACTCCTCCGTCTCCG) | 7% | 90% | 61.2° C. |
| Probe & Helper I & J | 18% | 91% | |
| Probe & Helper K (GCACGTGTGAAGCCCTGGTCGTAA- | 7% | 90% | 59.8° C. |

TABLE IIC-continued

| Reagent (& Sequence) | Percent Hybrid Found | | Tm |
|---|---|---|---|
| | Hybridization for 12 min. | Overnight Hybridization | |
| GGGCCATGAGGACTTGACGTCAT-CCCCACCTTCC) | | | |
| Probe & Helpers I & J & K | 17% | 91% | 67.8° C. |

The results in Tables IIA, B, and C further confirm the effect of using helper oligonucleotides on probe hybridization with a target nucleic acid, including the effect of helper oligonucleotides which bind at a region remote to the region bound by the probe. The ability of the helper oligonucleotides to raise the $T_m$ of the hybrid of probe and target nucleic acid is also further confirmed.

EXAMPLE 3

A DNA multimer target of 90 units was synthesized using a DNA synthesizer to have the following nucleotide sequence:

5'-TTCGGGTT|GTAAAGTACTTTCAGCGGGGAG-
Helper A Region
G|AAGGGAGTAAAGTTAATACCTTG|CTCAT
Probe Region
TGACGTTACCCGCAGAAGAAGCACC|GGCTA-3'
Helper B Region The DNA sequence was synthesized to have a nucleotide base sequence which corresponds to the region centered at about nucleotide 450 of the 16S ribosomal RNA of *E. coli*. A probe complementary to the region designated as the "probe region" was synthesized to have the following sequence:

5'-CAAAGGTATTAACTTTACTCCCTT-3'

Assays were run using the DNA 90-mer and the probe with and without Helpers A and B. For comparison purposes, similar assays were run using the rRNA of E.coli as target. The regions recognized by these helpers in Salmonella are conserved in the *E. coli* ribosome. The assays were run as described in Example 1 except that the molar ratio of each helper to probe was 250 to 1.

The percent hybridization observed in the assays between the probe and the rRNA of *E. coli* and the DNA 90-mer alone or with Helper A and B are shown in Table III.

TABLE III

| Target | Reagent | Overnight Hybridization % Hybrid Found |
|---|---|---|
| Control-no RNA or DNA | Probe alone | 0.6% |
| *E. coli* rRNA | Probe alone | 1.5% |
| *E. coli* rRNA | Probe/Helpers A & B | 85% |
| DNA 90-mer | Probe/alone | 2.85% |
| DNA 90-mer | Probe/Helpers A & B | 87% |

These results demonstrate that helper oligonucleotides also improve the kinetics of hybridization with a DNA target. Similar results were obtained at 37° C., the temperature of the human body, demonstrating that hybridization of probe to a nucleic acid is obtained under conditions which would permit in vivo applications of the helper oligonucleotides in, for example, hybridization arrest procedures.

EXAMPLE 4

Gonorrhea is one of the most commonly reported bacterial infections in the United States, with over two million cases reported annually. This sexually transmitted disease usually results in anterior urethritis in males and involves the cervix in females. While severe complications and even sterility can occur in untreated individuals, asymptomatic infections are common, resulting in carriers who unknowingly spread the disease.

The causative agent, *Neisseria gonorrhoeae*, is a gram negative, oxidase positive diplococcus with stringent growth requirements. The method used for diagnosis depends on the site of infection and the patient symptoms. Gonococcal urethritis in males is diagnosed with good sensitivity and specificity using gram stain. Culture, requiring 24-72 hours, usually must be performed to confirm diagnosis of gonorrhea from all females and asymptomatic males. Following the detection of the organism from growth in culture, *Neisseria gonorrhoeae* must be identified by further tests such as carbohydrate degradation, coagglutination, fluorescent antibody screens or chromogenic enzyme substrate assays.

*Neisseria gonorrhoeae* is particularly difficult to detect and distinguish using a nucleic acid probe because it is very closely related to *N. meningitidis*. Data published in Kingsbury, D. T., *J. Bacteriol.* 94:870-874 (1967) shows a DNA:DNA homology for the two species of approximately 80-94%. Under guidelines established by the Ad Hoc Committee on Reconciliation of Approaches to Bacterial Systematics, *Int'l J. System. Bacteriol.* 37:463-464 (1987), the phylogenetic definition of a species generally means 70% or greater DNA:DNA homology. Despite the fact that these organisms may be considered to be the same species under established principles, an assay was developed capable of distinguising them using helper oligonucleotides.

As expected, the rRNA homology between *N. gonorrhoeae* and *N. meningitidis* is even greater than the DNA homology between these species because of known conserved regions. A 1.0% difference between the 16S and a 1.1% difference between the 23S rRNA sequences of *N. gonorrhoeae* and *N. meningitidis* has been observed. See Hogan, et al., U.S. patent application having Ser. No. 099,392, filed Nov. 24, 1987 entitled "Nucleic Acid Probes for Detection and/or Quantitation of Non-Viral Organisms", the disclosure of which is incorporated herein by reference.

Making a probe for *N. gonorrhoeae* was complicated by the fact that in some sites where *N. meningitidis* and *N. gonorrhoeae* differed, other Neisseria species were similar to *N. gonorrhoeae*. The few mismatches which exist between these two species are in the most variable regions, i.e., regions which vary not only between species, but also from strain to strain. Despite the fact that some believed the species could not be distinguished at all, and others believed that rRNA was too conserved to be useful in probe diagnostics, Hogan, et al. describe probes capable of differentiating *N. gonorrhoeae* and *N meningitidis*.

The following sequences were characterized and shown to be specific for *Neisseria gonorrhoeae*. The phylogenetically nearest neighbors *Neisseria meningitidis, N. lactamica, N. cinerea, N. mucosa,* and *Kingella kingae* were used for comparison with the *N. gonorrhoeae* sequence.

1. CCG CCG CTA CCC GGT AC
2. TCA TCG GCC GCC GAT ATT GGC
3. GAG CAT TCC GCA CAT GTC AAA ACC AGG TA

Sequence 1, complementary to 16S rRNA in the region 125–150, is 17 bases in length and has a $T_m$ of 56° C. Sequence 2, complementary to 16S rRNA in the region 455–485, is 21 bases in length and has a $T_m$ of 63° C. Sequence 3, complementary to 16S rRNA in the region 980–1015, is 29 bases in length and has a $T_m$ of 57° C.

Oligonucleotides complementary to sequences adjacent to the probe regions were synthesized and mixed with probes and used in a hybridization procedure.

The reactivity and specificity of the probes for *Neisseria gonorrhoeae* was demonstrated with a hybridization assay. The three oligonucleotide probes were iodinated with $^{125}I$ and mixed with unlabeled oligonucleotides of sequence 5'-CCC CTG CTT TCC CTC TCT AGA CGT ATG CGG TAT TAG CTG ATC TTT CG-3', 5'-GCC TTT TCT TCC CTG ACA AAA CTC CTT TAC AAC CCG-3', 5'-GGC ACG TAG TTA GCC GGT GCT TAT TCT TCA GGT AC-3', and 5'-GGT TCT TCG CGT TGC ATC GAA TTA ATC CAC ATC ATC CAC CGC-3', and with purified RNA (target excess) in 0.48 M sodium phosphate, pH 6.8, 0.5% sodium dodecyle sulfate (SDS) and incubated at 60° C. for one hour. The helper to probe molar ratio was 60 to 1. Following incubation, 4 ml of 2% hydroxyapatite, 0.12 M sodium phosphate pH 6.8, 0.02% SDS was added and the mixture was incubated at 60° C. for 5 minutes. The samples were centrifuged and the supernatants were removed. Five ml of wash solution (0.12 M sodium phosphate pH 6.8, 2% SDS) was added and the samples were mixed, centrifuged, and the supernatants removed. The amount of radioactivity bound to the hydroxyapatite was determined in a gamma counter.

Table IV shows that the probes hybridize well to *N. gonorrhoeae* RNA and do not hybridize to the other species tested.

TABLE IV
HYBRIDIZATION OF NEISSERIA GONORRHOEAE
PROBES 1-3 TO NEISSERIA AND KINGELLA RNAS

| Organisms | ATCC # | % Probe Bound |
|---|---|---|
| Kingella kingae | 23332 | 0.09 |
| Neisseria cinerea | 14685 | 0.04 |
| N. gonorrhoea | 19424 | 48.4 |
| N. lactamica | 23970 | 0.07 |
| N. meninqitidis serogroup A | 13077 | 0.04 |
| N. meningitidis serogroup B | 13090 | 0.04 |
| N. meninoitidis serogroup C | 13102 | 0.04 |
| N. mucosa | 19696 | 0.07 |
| N. subflava | 14799 | 0.05 |

25

The foregoing experiments demonstrate the utility of helper oligonucleotides in increasing the rate and extent of hybrid formation between a probe and a target nucleic acid and the effect of raising the Tm of the resulting hybrids. In one embodiment of the invention, the helper oligonucleotides may be utilized in assays which use a DNA or RNA probe to detect DNA or RNA of interest in suitable samples.

The helper oligonucleotides can be used, for example, in assays which target DNA as described in U.S. Pat. No. 4,358,535. The DNA in that assay is fixed to a solid surface. However, a "soluble" portion which is not fixed to the solid phase does extend into the solvent medium containing the probe and to that extent can possess a secondary and tertiary structure like a fully solubilized, single strand of nucleic acid.

The helper oligonucleotides can also be used in assays which target rRNA as described in Canadian Patent No. 1,215,904 and mRNA as described in European Patent Application No. 84900667.1. These assays rely upon the separation of unhybridized probe using a solid phase which selectively removes the hybrid. It is also possible to use helper oligonucleotides in assays which are conducted in a homogeneous medium as described in Arnold, et al., application for U.S. patent Ser. No. 099,392, filed Sept. 21, 1987 entitled Homogeneous Protection Assay, the disclosure of which is incorporated herein.

In such assays, the probe can be labeled with any suitable label such as a radionucleotide, for example, $^{125}I$, $^{32}P$, $^{3}H$ or the like. The label can be an enzyme such as horseradish peroxidase or alkaline phosphatase which catalyzes a color forming reaction of a suitable substrate. The label may also be a fluorometric moiety. Most preferably the label is an acridinium ester such as described in British Patent No. 2,112,779B and Arnold, et al., supra.

In such assays, a single or multiple helpers may be used. Typically the helper is added in substantial molar excess compared to the amount of nucleic acid present in the sample in order to more rapidly bind to the target nucleic acid and inhibit intramolecular strands hybridizing, which impose the secondary and tertiary structure which inhibits probe to target hybridization.

The assays themselves are typically run at a temperature which is 4° to 5° C. below the $T_m$ of the probe:target hybrid. This reduces the extent of hybridization between the probe and nontarget DNA, thereby reducing the likelihood of a false positive result.

Since the helper oligonucleotides can be used in processes for detecting a target nucleic acid, the invention also contemplates a kit for use in such assays comprising one or more probes and one or more helper oligonucleotides as reagents. In such a kit the probe would be provided with a suitable label as described herein. Such a kit may also include positive and negative controls and standards for obtaining quantitative results.

In another embodiment of the invention, the helper oligonucleotides can also be used to enhance the in vivo hybridization of a probe with a target nucleic acid such as mRNA in hybridization arrest procedures. In such a case the probe and helper may be given a patient as a mixture or sequentially, the helper typically being administered first to establish a structure which will permit better binding between probe and target. Again, multiple helpers may be used. In such in vivo applications it is preferred to use a DNA analogue, such as a methylphosphonate, for both probe and helper as methylphosphonates and other analogues are known to enter a cell more easily than DNA with the usual phosphate diester backbone. In such a case, the probe and helpers may be administered in a suitable pharmaceutical carrier in an effective amount to cause hybridization arrest or other desired result. Administration may either be oral or parenterally.

The foregoing are but examples of the presently preferred embodiments of uses to which helper oligonucleotides of the present invention may be put. Accordingly, the present invention is to be considered limited only by the appended claims.

We claim:

1. A process for enhancing the binding between a nucleotide probe and a complementary nucleotide sequence in a single stranded target nucleic acid comprising adding to the target nucleic acid a helper oligonucleotide which hybridizes with the target nucleic acid in a different region than the probe, the helper oligonucleotide being added in an amount effective to enhance the binding of the probe to the target nucleic acid.

2. A process according to claim 1 wherein the target nucleic acid is selected from DNA, mRNA, rRNA and tRNA.

3. A process according to claim 2 wherein the target nucleic acid is separated from an organism producing it or in which it is found prior to the addition of the helper oligonucleotide and the nucleotide probe.

4. A process according to claim 2 wherein the helper oligonucleotide and the nucleotide probe are introduced to a cell in which the target nucleic acid is located and the hybridization between the target nucleic acid and the helper oligonucleotide and nucleotide probe occurs intracellularly.

5. A process according to any of claims 1, 2, 3 or 4 wherein the probe is a DNA oligonucleotide and the helper oligonucleotide is a DNA oligonucleotide.

6. A process according to claim 5 wherein the probe comprises from about 10 to about 50 nucleotides in length and the helper oligonucleotides comprise from about 10 to about 100 nucleotides in length.

7. A process according to claim 6 wherein the probe and helper oligonucleotides are selected from DNA having a diphosphate ester backbone, an alkyl or arylphosphonate backbone or a phosphorothioate backbone.

8. A process according to claim 7 wherein the probe comprises about 15 to about 40 nucleotides and the helper oligonucleotides comprise from about 20 to about 50 nucleotides.

9. A process according to claim 6 wherein the helper oligonucleotide binds with the target nucleic acid immediately adjacent to the probe.

10. A process according to claim 7 wherein the helper oligonucleotide binds with the target nucleic acid immediately adjacent to the probe.

11. A process according to claim 6 wherein the helper oligonucleotide binds with the target nucleic acid in a region removed from the probe.

12. A process according to claim 7 wherein the helper oligonucleotide binds with the target nucleic acid in a region remote from the probe.

13. A process according to claim 5 wherein the probe is labeled to permit the detection of the probe.

14. A process according to claim 13 wherein the probe is detected after formation of hybrid and separation from the unhybridized probe.

15. A process according to claim 14 wherein the label is a radionucleotide, an enzyme, a fluorometric moiety or a moiety which participates in a reaction which produces chemiluminescence.

16. A process according to claim 15 wherein the label is elected from $^{125}I$ or an acridinium ester.

17. A process according to claim 5 wherein a mixture of helper oligonucleotides is used.

18. A process according to claim 6 wherein a mixture of helper oligonucleotides is used.

19. A process according to claim 14 wherein a mixture of helper oligonucleotides is used.

20. A process according to claim 15 wherein a mixture of helper oligonucleotides is used.

21. A hybrid nucleic acid comprising a hybrid of a nucleotide probe and a target nucleic acid to which is hybridized a helper oligonucleotide.

22. A hybrid according to claim 21 wherein the duplex is comprised of more than one helper oligonucleotide.

23. A kit for the detection of a target nucleic acid comprising a labeled nucleotide probe complementary to a nucleotide sequence in the target nucleic acid and a helper oligonucleotide.

24. A kit according to claim 23 comprising two or more helper oligonucleotides.

25. A kit according to claim 24 wherein the kit contains two or more probes and two or more helper oligonucleotides.

26. A kit according to claim 25 wherein each probe has a helper oligonucleotide.

27. A kit according to claim 26 wherein one or more probes has two or more helper oligonucleotides.

* * * * *